United States Patent [19]

Cavaterra et al.

[11] Patent Number: 4,587,230

[45] Date of Patent: May 6, 1986

[54] SUPPORTED CATALYSTS FOR THE SYNTHESIS OF 1,2-DICHLOROETHANE BY OXYCHLORINATION OF ETHYLENE WITHIN A FLUIDIZED BED AND METHOD FOR THE PREPARATION OF THE CATALYSTS

[75] Inventors: Enrico Cavaterra, Saronno; Alessandro Bossi, Novara, both of Italy

[73] Assignee: Montepolimeri S.p.A., Milan, Italy

[21] Appl. No.: 742,238

[22] Filed: Jun. 7, 1985

Related U.S. Application Data

[63] Continuation-in-part of Ser. No. 591,993, Mar. 21, 1984, abandoned.

[30] Foreign Application Priority Data

Mar. 22, 1983 [IT] Italy ................................ 20198 A/83

[51] Int. Cl.$^4$ ......................... B01J 21/04; B01J 21/08; B01J 21/12; B01J 27/10
[52] U.S. Cl. .................................. 502/225; 502/244; 502/346
[58] Field of Search ....................... 502/225, 244, 346; 570/245

[56] References Cited

U.S. PATENT DOCUMENTS 4,124,534 11/1978 Leitert et al. ...................... 502/225
4,323,716 4/1982 Canavesi et al. .............. 570/245 X

FOREIGN PATENT DOCUMENTS 971996 10/1964 United Kingdom ............... 570/245

Primary Examiner—W. J. Shine

[57] ABSTRACT

A supported catalyst for the $C_2H_4$ oxychlorination within a fluidized bed comprising a Cu compound in amounts corresponding to a content from 1 to 10% by weight—as Cu metal—on a carrier preferably selected from the group consisting of microspheroidal $Al_2O_3$, microspheroidal $SiO_2$ and microspheroidal silica-alumina, characterized in that the molar ratio (outer Me/outer Cu), as determined by means of XPS analysis, is at least 40% higher than the molar ratio:

$$Y = \frac{\text{total Me present within the catalyst}}{\text{total Cu present within the catalyst}}$$

wherein Me is e.g., Al, Si or Al + Si.

The invention concerns a supported catalyst for the synthesis of 1,2-dichloroethane, hereinafter DCE, achieved by ethylene oxychlorination, said catalyst being used in the form of a fluidized bed.

9 Claims, 2 Drawing Figures

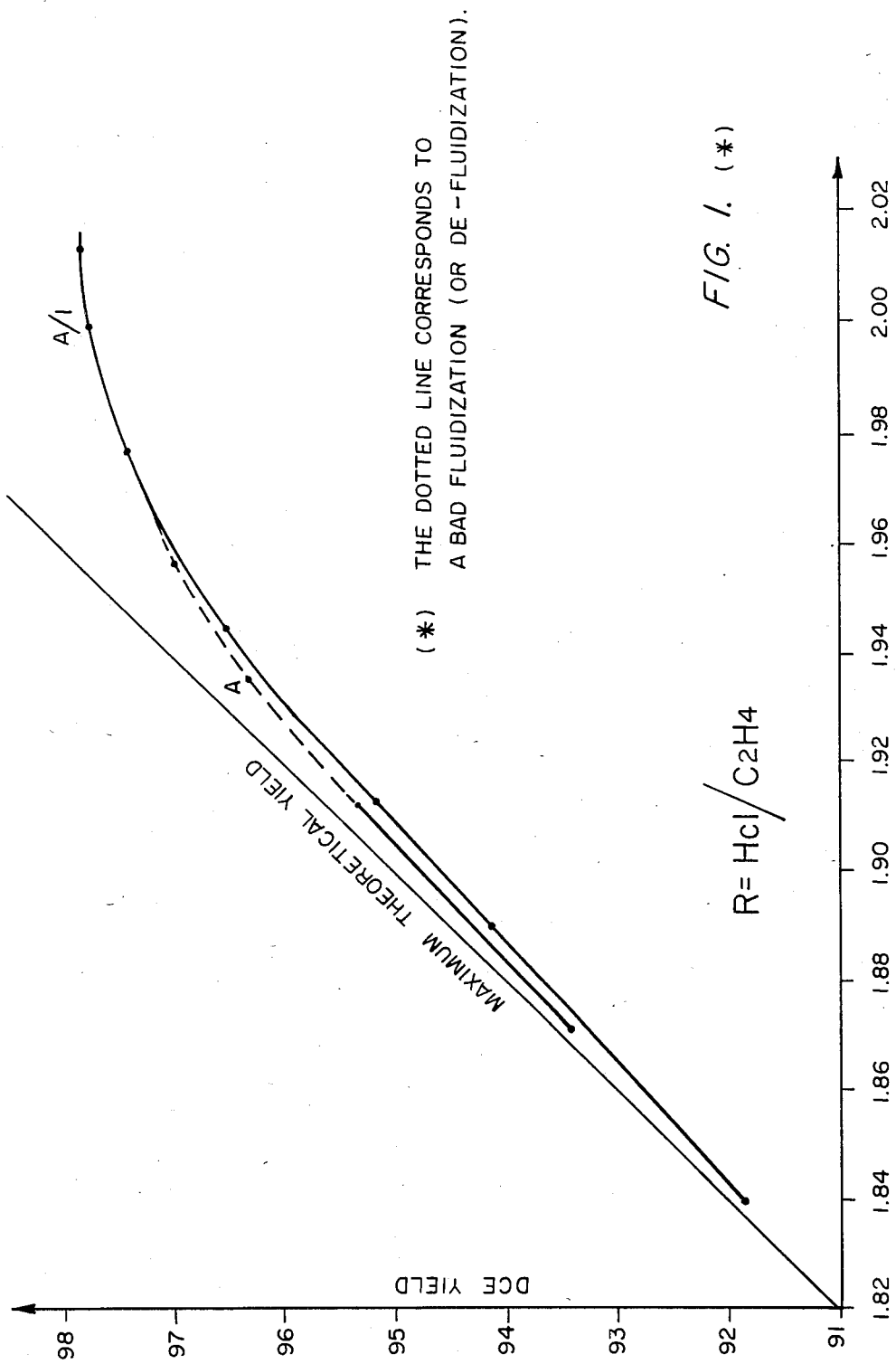

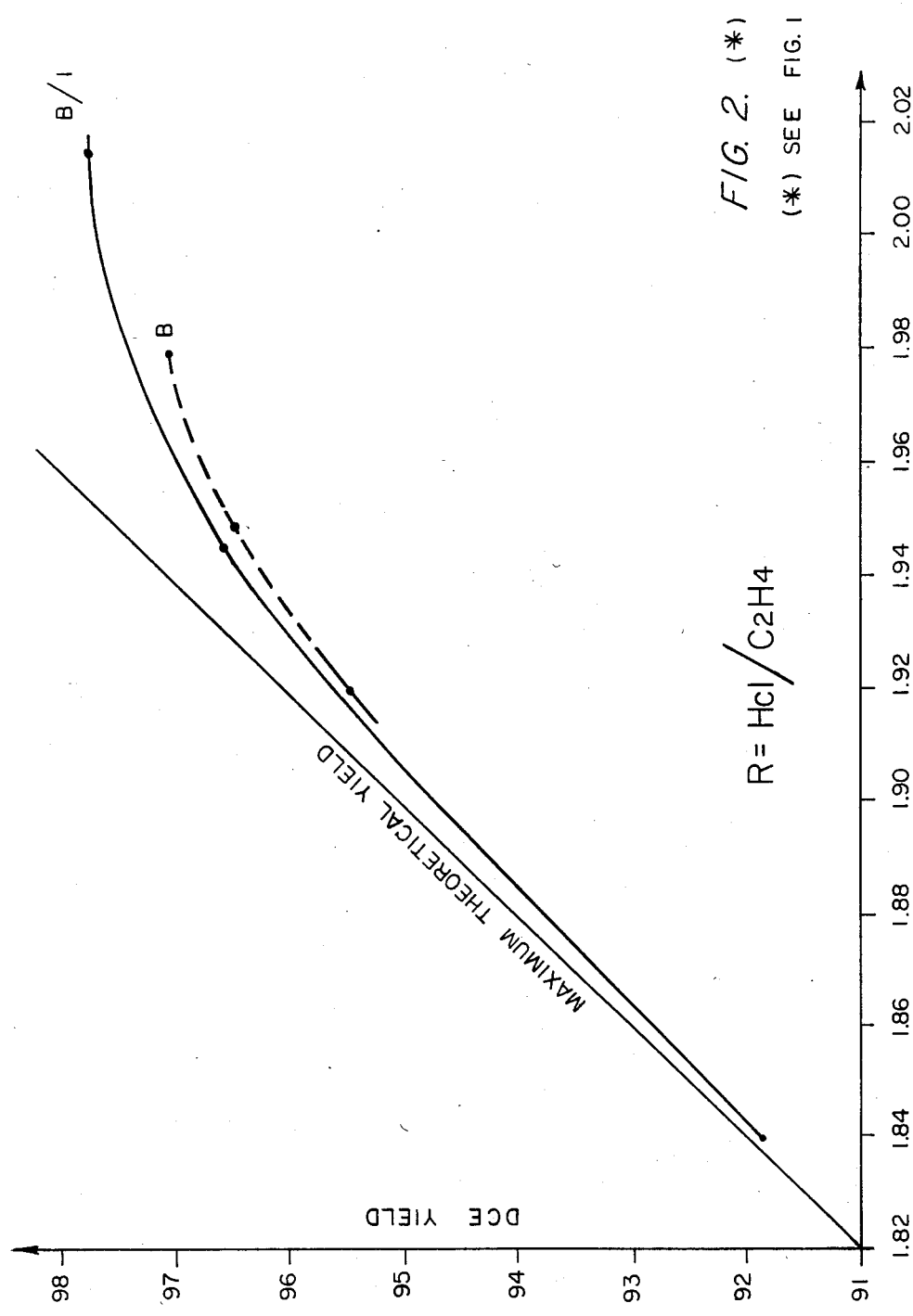

SUPPORTED CATALYSTS FOR THE SYNTHESIS OF 1,2-DICHLOROETHANE BY OXYCHLORINATION OF ETHYLENE WITHIN A FLUIDIZED BED AND METHOD FOR THE PREPARATION OF THE CATALYSTS

This application is a continuation-in-part of our application Ser. No. 591,993 filed Mar. 21, 1984, now abandoned.

BACKGROUND OF THE INVENTION

The catalytic gaseous phase oxychlorination of $C_2H_4$ with HCl and $O_2$ (or gases containing same) is quite known and was widely used for the preparation of DCE, from which, in a subsequent stage (by pyrolysis), vinyl chloride is obtained.

Likewise it is known to use the catalytic mass in the form of a fluidized bed, in order to get rid of the considerable heat released by both the oxychlorination reaction and the combustion of ethylene to CO and $CO_2$; the fluidized-bed processes which realized conditions of almost a perfect isothermicity are those which so far have met the greatest success.

Catalytic compositions promoting the oxychlorination have been described. The most common one is based on copper compounds, in general chlorides, supported in different amounts on microspheroidal supports (in general $Al_2O_3$) suited, for their granulometric distribution and resistance to friction wear, for use in fluidized beds. The previously described compositions show, however, many drawbacks which limit, and in certain instances hinder, a satisfactory exploitation on an industrial scale. Thus, for instance, there are catalytic formulations characterized by high DCE yields with respect to HCl, which must work, however, with a high $C_2H_4$ excess, with respect to HCl, in order to avoid the occurrence of bad fluidization phenomena (at the limit defluidization), wherefore the DCE yields, with respect to ethylene, are rather unsatisfactory. The $C_2H_4$ excess, with respect to DCE, cannot, in fact, be converted into DCE and is therefore eliminated with the gaseous exhausts as unreacted $C_2H_4$ or in the form of carbon oxides (CO and $CO_2$).

On the other hand, there are compositions which can work with a lower excess of $C_2H_4$, with respect to HCl, without meeting particular problems of bad fluidization of the catalytic bed, thus operating with high DCE yields with respect to $C_2H_4$, but which, on the contrary, lead to low HCl conversions. In the latter case, it is necessary to use a special equipment, withstanding HCl, in order to avoid corrosion; moreover, it is necessary to neutralize the unconverted HCl with alkali, with a consequential increase in technical burdens. Moreover, there are compositions characterized by the use of carriers different from $Al_2O_3$, for instance $SiO_2$ or silica-alumina, or by the presence in the catalyst, together with $CuCl_2$, of other compounds, in general chlorides, of alkali or alkaline-earth metals and of rare earths.

Italian Pat. No. 690,193 teaches the use of compositions based on $CuCl_2$, alkaline-earth chlorides and rare earth chlorides, in order to reduce the magnitude of the combustion on a fluidized bed. Likewise, British Pat. No. 971,996 exemplified catalytic compositions based on $CuCl_2$ and alkaline-earth chlorides on either a fixed or fludized bed. None of these compositions has been completely free of all the drawbacks, with respect to a satisfactory industrial exploitation, namely:

an insufficient DCE yield, with respect to $C_2H_4$;
an insufficient conversion of HCl;
a poor fluidization (at the limit de-fluidization).

In order to better appreciate the importance of these drawbacks and, consequently, the importance of their removal, it may be useful to provide more specific information as to the bad fluidization phenomena typical for the catalysts described so far. The reaction may be represented as follows:

$$C_2H_4 + 2HCl + \tfrac{1}{2}O_2 = Cl\!-\!CH_2CH_2\!-\!Cl + H_2O,$$

which means that in order to obtain a 100% DCE yield with respect to $C_2H_4$, one must feed, besides oxygen, a mixture of HCl and $C_2H_4$ in a molar ratio of at least 2. Thus, for instance, if one feeds HCl and $C_2H_4$ to the reactor in a 1.86 molar ratio, the maximum theoretical DCE yield, with respect to $C_2H_4$, is: $1.86:2\times100=93$. The yields that can be obtained are usually below this value, because of an incomplete conversion of HCl. In fact, considering:

$R = HCl/C_2H_4$ molar feed ratio;

$C = \%$ of conversion of HCl =

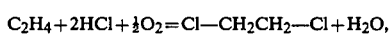

$$\left(1 - \frac{\text{HCl moles at outlet}}{\text{HCl moles at inlet}}\right) \times 100,$$

it is shown that the DCE yield, with respect to ethylene, is well approximated by the equation: DCE yield$=R/2\times C$, so that, in order to obtain high yields, R and C must be both as high as possible. Within a fluidized-bed reactor, consisting of a catalyst based on $CuCl_2$ supported on microspheroidal $Al_2O_3$, prepared according to the known technologies, the following phenomena take place:

with $HCl/C_2H_4$ feed ratios relatively low (e.g., lower than 1.9 mols) the fluidization is good, for the reasons hereinabove, the DCE yields, with respect to ethylene, are limited (e.g., below 95%).

increasing the $HCl/C_2H_4$ ratio above the previously indicated values, the fluidization worsens and the HCl conversion decreases. Such worsening can be perceived visually in pilot glass reactors and reveals itself by the formation of an increasing number of gas bubbles of growing diameter. When the diameter of the bubbles equals roughly the diameter of the reactor, the "rupture" of the catalytic bed can occur, namely there can be seen inside the bed, the formation of "empty" zones, alternated by "full" zones. Under extreme conditions, the catalyst is dragged out of the reactor.

In industrial reactors the worsening reveals itself in a less striking but still evident way through the enormous loss of catalyst in the cyclones, due to the clogging of the cyclones' legs, which hinders the flowing back, into the catalyst bed, of the catalyst separated at the head of the cyclones. In both cases, it is impossible to carry out normal operations and it is necessary to decrease the $HCl/C_2H_4$ feed ratio until a good fluidization is restored or, in extreme cases, to switch off the feed of the reactants.

The causes of these phenomena have been generically ascribed to the so called "stickiness", that hinders the free moving or reciprocal creep of the single granules, within the catalytic bed, because of the formation of clots that are difficult to fluidize (and give rise to the bubbles) and slightly flowable (hence the clogging of the cyclones' legs).

The sticking can be observed only in connection with the increase of the $HCl/C_2H_4$ feed ratio and is reversible; all this could mean that what is responsible for said phenomena is the active part of the catalyst, namely Cu (rather than the carrier, whose features are not substantially dependent on said ratio). In fact if we analyze the results of many kinetic works, we trace namely always a mechanism involving:

1. the reaction of $C_2H_4$ with $Cu_2Cl_4$, in order to give DCE and $Cu_2Cl_2$;
2. the oxidation of $CuCl_2$ with $O_2$ (air), to give $Cu_2OCl_2$;
3. the reaction of 2HCl with $Cu_2OCl_2$ to give again $Cu_2Cl_4$ and $H_2O$.

In other words Cu shifts cyclically from $Cu_2Cl_4$ (chlorided Cu) to $Cu_2Cl_2$ (reduced Cu) to $Cu_2OCl_2$ (oxychlorided Cu) and at last again to $Cu_2Cl_4$. The equilibrium between such forms depends essentially on the $HCl/C_2H_4$ feed ratio. When the ratio is growing, the chlorided form becomes prevailing, while at low values of said ratio the oxychlorided form is prevailing.

The occurrence of the sticking may thus be explained by a predominance of $Cu_2Cl_4$ with increasing $HCl/C_2H_4$ ratio; on the other hand, there is evidence of the trend of of $Cu_2Cl_4$ to form polymers [Kenney C. N., Catal. Rev. Sci. Eng. 11 (2), 197 (1975)]:

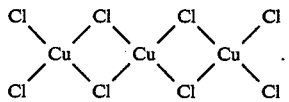

One solution of the problems is suggested by Italian Patent Publication No. 25,941 A/81. There is described a method for the preparation of a catalyst free from the drawbacks typical of the catalysts previously described. Said method comprises the impregnation of a preformed catalyst, consisting of $CuCl_2$ supported on $Al_2O_3$, by means of an aqueous solution of $MgCl_2$, whereupon the catalyst is dried and activated in air at temperatures up to 300° C.; in spite of the excellent performance of this catalyst, it is useful to manufacture catalysts showing even better features.

OBJECT OF THE INVENTION

One object of the present invention is that of providing, in the most simple and effective way, a catalyst for the $C_2H_4$ oxychlorination to DCE, suited for use in fluidized beds, displaying the best features required for a satisfactory industrial exploitation, namely:

a high DCE yield, with respect to $C_2H_4$;
a high conversion of HCl;
excellent fluidization features.

Still other objects will become evident from the following description.

DESCRIPTION OF THE INVENTION

The invention concerns a supported catalyst for the synthesis of 1,2-dichloroethane (by means of $C_2H_4$ oxychlorination within a fluidized bed) comprising a Cu compound in amounts corresponding to a content from 1 to 10% by weight, preferably 3.8% by weight—as Cu metal—on a carrier selected from the group consisting of microspheroidal $Al_2O_3$, microspheroidal $SiO_2$ and microspheroidal silica-alumina, characterized in that the molar ratio $$MR = \frac{\text{Outer Me}}{\text{Outer Cu}},$$

as determined by XPS analysis is at least 40% higher than the molar ratio:

$$Y = \frac{\text{total Me present within the catalyst}}{\text{total Cu present within the catalyst}}$$

wherein Me is Al, Si or Al+Si (or other metal present in the carrier) and wherein, therefore, $MR/Y \geq 1.40$.

As described hereinafter, the XRS analysis technique allows the analysis of a surface layer having a thickness from 2 to 3 nanometers (nm).

Preferably the molar ratio (outer Me/outer Cu) is equal to or higher than 20:1 and the Cu concentration on the outer surface of the carrier is zero or, in any case, much lower than the Cu concentration in the layers immediately underlying the analyzed surface layer. Interesting results were obtained with a ratio (outer Me/outer Cu) between 40:1 and 53:1. Said catalysts comprise advantageously also a Mg compound, the Mg amounts being usually from 0.2 to 0.8 moles of Mg per mole of Cu.

In order to obtain a catalyst characterized by low Cu concentration on the outer surface of the granules and having, as such, the features required for a satisfactory industrial exploitation, the following methods can be employed, particularly the following two methods: (I) The first method is characterized in that a preformed catalyst of the usual type, based on $CuCl_2$ supported on $Al_2O_3$, is impregnated in its dry state with an aqueous solution (of a volume substantially equal to the volume of the pores of the carrier), containing a strong acid, for instance HCl, in amounts corresponding to at least 1 equivalent per mole of Cu (present in the catalyst) and preferably containing also $MgCl_2$ in amounts from 0 to 1 mole per mole of Cu (present in the catalyst), the catalyst being preferably dried (e.g., at 110° C.) after impregnation, and subsequently activated in air (e.g., for 4 hours between 180° and 300° C.). In this way, it is possible to obtain a catalyst from the outer surface of which the major portion of Cu (present in the starting pre-formed catalyst) is removed.

(II) The second method is characterized in that a carrier is impregnated in the dry state with an aqueous solution (of a volume substantially equal to the volume of the pores of the carrier) containing a Cu compound, in such an amount to load into the final catalyst a Cu amount, expressed as metal, from 1 to 10% by weight, and containing, moreover, an acid and a Mg compound, in amounts equal to at least 1 equivalent of acid and from 0 to 1 mole, more specifically from about 0.2 to 1 moles, of Mg per mole of Cu, the catalyst being dried preferably after impregnation, and then being activated in air at between 180° and 300° C.

Also in this case it is possible to obtain a catalyst on the outer surface of which the Cu content is kept at a minimum. The Mg compound corresponds preferably to the Cu compound in the sense that, for instance, in the case salts are used, the Mg salt derives from the same acid from which the Cu salt is derived. Analogously, said salt must correspond to the Cu compound. If the Cu compound is $CuCl_2$, the acid will thus be HCl while the Mg compound will be $MgCl_2$.

The catalyst according to the invention is characterized by a minimum or no (and at any rate definitely lower than that of the catalysts already described) concentration of Cu on the outer surface of the granule, as it results from the determinations carried out with the technique known as X-Ray Photoemission Spectroscopy (henceforth XPS), and, as such, displays excellent fluidization features and maintain high HCl conversions, also in the case of high HCl/$C_2H_4$ ratios, so that it is possible to achieve high DCE yields with respect to $C_2H_4$.

The inner Cu, although involved in the conversion cycles and in the equilibria between the various forms ($Cu_2Cl_2$, $Cu_2Cl_4$, etc.), depending on the HCl/$C_2H_4$ feed ratio, does not give place to the sticking phenomena which, on the contrary, involve the zones of possible contact between the different granules.

The main feature of the catalyst according to the invention is that the active part is almost completely segregated inside of the pores of the carrier, wherefore the Cu concentration on the outer surface is at a minimum, and any way lower than that of conventional catalysts, as shown by XPS measures, and at said minimum the concentration remains also after long stretches of time.

The use of this catalyst allows to conduct the reaction within a fluidized bed, using, without any bad fluidization, high HCl/$C_2H_4$ ratios in the feed and (particularly when the catalyst contains Mg) high conversions of HCl and high DCE yields (with respect to $C_2H_4$) are thus obtained, in accordance with the equation: yield of $DCE = R \times C/2$.

The operating oxychlorination conditions do not substantially differ from those typical for the catalysts previously described.

$C_2H_4$, HCl and gases containing $O_2$ (in general air), are fed in gaseous phase, are then pre-heated up to a temperature from 200° to 250° C., preferably from 220° to 235° C.

The other operative parameters, in general, are comprised between the following ranges:

(A) Air/$C_2H_4$ ratio: such that the $O_2$ content, in the gaseous exhausts, after condensation of DCE, $H_2O$ and HCl, be from 3 to 10% by volume.

(B) HCl/$C_2H_4$ ratio: the nearest possible to the stoichiometric value (2/1 molar), compatibly with the saving of good fluidization conditions of the catalytic bed and of a sufficiently high conversion of HCl, conditions which depend on the type of catalyst.

(C) Contact time (expressed as a ratio between the volume of the catalytic bed in a fluidized state, and the volumetric flow rate of the mixture of reactants, at the temperature and pressure conditions existing in the catalytic bed): it depends essentially on the type of the catalyst; in general it is from 10 to 40, preferably from 20 to 30 seconds.

(D) Linear velocity of the gases: within the range between the minimum fluidization rate and the dragging speed, both being typical for each type of catalyst; in general said velocity is from 10 to 50, preferably from 20 to 40 cm/s.

(E) Total pressure during the reaction (relevant for achieving an effective contact between the reactants, in a gaseous phase, and the catalyst, in a solid phase); in general pressures greater than atmospheric and up to 600 KPa are used; at greater pressures, energy waste becomes predominant, due to the compression work.

The following examples are given for purely illustrative and not limiting purposes.

OPERATIVE CONDITIONS COMMON TO DIFFERENT EXAMPLES

The catalysts cited in the examples (except preformed catalyst 'A') were prepared by impregnation in the dry state with an aqueous solution, dried at 110° C. and activated in air for 4 hours at the temperature (either 180° or 300° C.) indicated in Table 1, which reports also the results of the XPS analysis. The measurements of the outer surface concentration of Cu were carried out following the XPS technique (see C. D. Wagner: "Handbook of X-ray Photoemission Spectroscopy"; Perkin Elmer Co., Eden Prairie; 1979), based on X-ray irradiation and on measuring of the energy level and of the energy intensity of the electrons emitted by the solid. The energy level of said electrons is characteristic for the element while the energy intensity is proportional to the number of atoms present in the volume of sample, down to a depth substantially from 2 to 3 nm (20–30 Å) from the surface. As the mean granulometric size of the catalyst lies around 50 $\mu m$ (micrometers), usually ranges from 20 to 80 $\mu m$ are cited. The measures of the atomic concentrations refer to about 1 tenthousandth of the diameter of the granule, namely, essentially, to its outer surface. A small amount of a sample (just a few mg) was pressed onto a pure indium plate in order to obtain an analyzable surface of an area equivalent to a few sq.mm. The samples were then analyzed under a high-pushed vacuum, at a basic pressure of $2 \times 10^{-7}$ Pa, using an X-ray source operating at 400 W and fitted with a Mg-anode (K$\alpha$ radiation of magnesium). The photoemission spectra of the present elements, that is O/1s, C/1s, Cl/2p, Mg/2p, Al/2p, were then gathered together under conditions of high resolution with the help of a computer suited for the digitalized acquisition of the data, with a maximation of the signal noise ratio. After the removal of the background noise, the areas of the photoemission peaks were calculated by means of numerical integration; the intensity value thus obtained, corrected for the respective sensitivity factor, was directly proportional to the surface atomical concentration of the respective element.

Therefore, it is possible to calculate the molar ratio $$\frac{\text{Outer Al}}{\text{Outer Cu}}$$

within a layer having substantially a thickness of 2–3 nm (20–30 Angstrom). Clearly, such ratio is equal to the ratio:

$$\frac{\text{surface atomical concentration of Al}}{\text{surface atomical concentration of Cu}}$$

The same applies if $SiO_2$ is the carrier instead of $Al_2O_3$, for the ratio $$\frac{\text{Outer Si}}{\text{Outer Cu}}$$

or more broadly, for the molar ratio $$MR = \frac{\text{Outer Me}}{\text{Outer Cu}}$$

M being Al, Si or Al+Si.

BRIEF DESCRIPTION OF THE DRAWINGS

In the accompanying drawings:

FIG. 1 is a graph in which the $HCl/C_2H_4$ ratio is plotted against the DCE yield for catalyst A/1, line curve representing "bad" fluidization or de-fluidization; and FIG. 2 is a graph in which the $HCl/C_2H_4$ ratio is plotted against the DCE yield for catalyst B/1, the dotted line curve having the same significance as in FIG. 1.

EXAMPLES from 1 to 6

(Preparation of the Catalyst)

Catalyst 'A' is a usual (commercially available) preformed comparison catalyst, based on $CuCl_2$, supported on a microspheroidal alumina carrier, having a Cu content (as a metal) of 5% by weight, while comparison catalyst 'B' was prepared by impregnation in the dry state of a carrier (consisting of microspheroidal alumina with a mean particle diameter of 50 $\mu$m) with an aqueous solution (with a volume equal to the volume of the pores of the carrier) containing $CuCl_2$, thereby obtaining a catalyst with a final Cu content (expressed as a metal) of 5% by weight. The outer coating degree can be better represented by the Al/Cu ratio which, independently from possible variations in the corresponding amounts of oxygen and chlorine, gives the "frequency" of Cu atoms with respect to Al atoms. In this way, the outer surface of catalysts A and B is characterized by the presence of a Cu atom every 10 Al atoms, as pointed out in Table 1.

Catalyst 'A/1' was prepared by impregnating in the dry state catalyst 'A' with an aqueous solution (of a volume equal to the volume of the pores of the catalyst), and containing 2 moles of HCl and 0.75 moles of $MgCl_2$ per mole of Cu (contained in the catalyst); according to Table 1, the outer surface Cu is reduced fourfold (4 times) with respect to catalyst A.

Catalyst 'B/1' was prepared by impregnating in the dry state the carrier used for preparing catalyst B with an aqueous solution (of a volume equal to the volume of the pores of the carrier). Said solution contained:

$CuCl_2$ in such an amount to obtain 5% by weight of Cu on the global weight of the catalyst;
2 moles of HCl per mole of Cu;
0.75 moles of $MgCl_2$ per mole of Cu.

According to Table 1, catalysts B/1 have an outer surface Cu concentration reduced four to fivefold with respect to catalyst B. The most meaningful ratios are summarized hereinbelow.

| Ex. | Catalyst | X = outer Al / outer Cu (by moles) | Y = total Al / total Cu (by moles) | $K = \frac{X - Y}{Y} \times 100$ |
|---|---|---|---|---|
| 1 (*) | A (*) | 10 | 22.3 | Negative (−55.16%) |
| 2 (*) | B (*) | 10 | 22.3 | Negative (−55.16%) |
| 3 | A/1 | 40 | 22.3 | 44.25% |
| 4 | A/1 | 40 | 22.3 | 44.25% |
| 5 | B/1 | 45 | 22.3 | 50.44% |
| 6 | B/1 | 53 | 22.3 | 57.92% |

(*) Comparative.

TABLE 1

| Ex. No. | Catalyst | Activation temperature T (°C.) | % of atoms on external surface | | | | Al/Cu |
|---|---|---|---|---|---|---|---|
| | | | Cu | Cl | Al | O | |
| 1 | A (*) | — | 3.0 | 4.4 | 32.4 | 60.2 | 10 |
| 2 | B (*) | 180 | 3.8 | 4.9 | 38.8 | 52.4 | 10 |
| 3 | A/1 | 180 | 0.9 | 3.8 | 36.0 | 59.3 | 40 |
| 4 | A/1 | 300 | 1.0 | 4.0 | 40.0 | 55.0 | 40 |
| 5 | B/1 | 180 | 0.8 | 4.6 | 35.4 | 59.2 | 45 |
| 6 | B/1 | 300 | 0.7 | 4.2 | 37.0 | 58.1 | 53 |

(*) Comparison samples.

EXAMPLES from 7 to 26

(Behavior of the Catalyst)

Into a glass reactor having a diameter of 4 cm and a height of 3 mt., suited for withstanding pressures up to 600 Kpa, were introduced the prepared catalysts and they were then tested in the form of a fluidized bed (in the oxychlorination of $C_2H_4$) under the following conditions: P=4 absolute atm.; contact time: 28 sec.; air/$C_2H_4$=3.2 (by moles). The values of oxychlorination temperature and of the ratio R=$HCl/C_2H_4$, are reported in Table 2, beside the results.

Examples 7 to 16 show that, in correspondence to the lower concentrations of outer surface Cu, the better fluidization features of catalysts A/1 allow to operate at higher $HCl/C_2H_4$ ratios, as to provide better DCE yields with respect to catalyst A. The comparison becomes even more evident from the graph in FIG. 1. The same may be said for Examples 17 to 26 and therefore for the excellence of catalysts B/1 with respect to catalyst B (See FIG. 2).

TABLE 2

| Example No. | Catalyst | Al/Cu | Activation Temperature T (°C.) | Oxychlorination T (°C.) | $HCl/C_2H_4$ (by moles) | DCE yield (molar % on fed $C_2H_4$) | HCl Conversion (%) | Fluidization |
|---|---|---|---|---|---|---|---|---|
| 7 | A | 10 | — | 220 | 1,871 | 93,45 | 99,89 | Good |
| 8 | A | 10 | — | 220 | 1,913 | 95,35 | 99,69 | Good |
| 9 | A | 10 | — | 220 | 1,936 | 96,35 | 99,53 | Bad |
| 10 | A | 10 | — | 220 | 1,958 | 97,00 | 99,08 | Defluidizes |
| 11 | A/1 | 40 | 180 | 225 | 1,844 | 91,90 | 99,89 | Excellent |
| 12 | A/1 | 40 | 180 | 225 | 1,936 | 96,25 | 99,40 | Excellent |
| 13 | A/1 | 40 | 180 | 225 | 2,014 | 97,80 | 97,12 | Good |
| 14 | A/1 | 40 | 300 | 225 | 1,889 | 94,20 | 99,70 | Excellent |
| 15 | A/1 | 40 | 300 | 225 | 1,945 | 96,55 | 99,28 | Excellent |
| 16 | A/1 | 40 | 300 | 225 | 2,016 | 97,70 | 96,93 | Good |
| 17 | B | 10 | 180 | 220 | 1,920 | 95,47 | 99,54 | Good |
| 18 | B | 10 | 180 | 220 | 1,980 | 97,05 | 98,10 | Bad |
| 19 | B | 10 | 180 | 220 | 2,029 | — | — | Defluidizes |
| 20 | B/1 | 45 | 180 | 225 | 1,840 | 91,90 | 99,83 | Excellent |
| 21 | B/1 | 45 | 180 | 225 | 1,889 | 94,20 | 99,75 | Excellent |
| 22 | B/1 | 45 | 180 | 225 | 1,945 | 96,59 | 99,30 | Excellent |
| 23 | B/1 | 45 | 180 | 225 | 2,016 | 97,68 | 96,90 | Good |
| 24 | B/1 | 53 | 300 | 225 | 1,936 | 96,24 | 99,40 | Excellent |

TABLE 2-continued

| Example No. | Catalyst | Al/Cu | Activation Temperature T (°C.) | Oxychlorination T (°C.) | HCl/C₂H₄ (by moles) | DCE yield (molar % on fed C₂H₄) | HCl Conversion (%) | Fluidization |
|---|---|---|---|---|---|---|---|---|
| 25 | B/1 | 53 | 300 | 225 | 2,014 | 97,86 | 97,20 | Good |
| 26 | B/1 | 53 | 300 | 225 | 2,089 | 97,93 | 93,80 | Good |

What is claimed is:

1. A supported dry-impregnated catalyst for the synthesis of 1,2-dichloroethane by $C_2H_4$ oxychlorination within a fluidized bed, said catalyst containing 1% to 10% by weight of Cu, with respect to the whole catalyst, and a carrier selected from the group consisting of microspheroidal $Al_2O_3$, microspheroidal $SiO_2$ and microspheroidal silica-alumina, and being characterized in that the molar ratio $$MR = \frac{\text{Outer Me}}{\text{Outer Cu}}$$

as determined by XPS analysis is at least 40% higher than the molar ratio:

$$Y = \frac{\text{total Me present within the catalyst}}{\text{total Cu present within the catalyst}}$$

wherein Me is Al, Si or Al+Si and wherein, therefore, $MR/Y \geq 1.40$.

2. A catalyst according to claim 1 containing 3 to 8% by weight of Cu.

3. A catalyst according to claim 1, in which the MR ratio is equal to or higher than 20:1.

4. A catalyst according to claim 1, in which there is no Cu concentration on the outer surface of the carrier or the concentration is much lower than the Cu concentration in the layers immediately underlying the surface layer, said surface layer having substantially a thickness of 2-3 nm.

5. A catalyst according to claim 1, wherein said catalyst also contains Mg, the Mg amount being from 0.2 to 1.0 mole per mole of Cu.

6. A method for the preparation of a catalyst according to claim 1, characterized in that a preformed catalyst based on $CuCl_2$ supported on $Al_2O_3$, $SiO_2$ or silica-alumina, is impregnated in the dry state with an aqueous solution having a volume substantially equal to the volume of the pores of the carrier and containing a strong acid in amount corresponding to at least 1 equivalent per mole of Cu present in the catalyst, said acid solution containing also a Mg compound in amounts from about 0.2 to 1.0 mole of Mg per mole of Cu present in the catalyst drying and activating said catalyst.

7. A method for the preparation of a catalyst according to claim 1, characterized in that a carrier is impregnated in the dry state with an aqueous solution having a volume substantially equal to the volume of the pores of the carrier and containing a Cu compound in such amount as to produce, in the final catalyst, a Cu content, expressed as a metal, of from 1 to 10% by weight, and also containing an acid and a Mg compound, in amounts equal to at least 1 equivalent of acid and between about 0.2 and 1.0 mole of Mg, per mole of Cu, respectively, drying and activating said catalyst.

8. A method according to claim 7, wherein said Cu and Mg compounds are salts and the Mg salt derives from the same acid as the Cu salt.

9. A method according to claim 8, wherein the Cu compound is $CuCl_2$, the acid is HCl and the Mg compound is $MgCl_2$.

* * * * *